United States Patent
Shecterle

(10) Patent No.: US 9,006,507 B2
(45) Date of Patent: *Apr. 14, 2015

(54) PROCESS FOR ISOMERIZING A FEED STREAM INCLUDING ONE OR MORE C4-C6 HYDROCARBONS

(71) Applicant: UOP LLC, Des Plaines, IL (US)

(72) Inventor: David J. Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/191,049

(22) Filed: Feb. 26, 2014

(65) Prior Publication Data

US 2014/0179974 A1    Jun. 26, 2014

Related U.S. Application Data

(62) Division of application No. 13/005,940, filed on Jan. 13, 2011, now Pat. No. 8,692,046.

(51) Int. Cl.
C07C 5/27 (2006.01)
C10G 45/62 (2006.01)

(52) U.S. Cl.
CPC .............. *C07C 5/2754* (2013.01); *C10G 45/62* (2013.01); *C10G 2300/104* (2013.01); *C10G 2300/305* (2013.01); *C10G 2400/02* (2013.01)

(58) Field of Classification Search
USPC .......................................... 585/734, 736, 738
See application file for complete search history.

(56) References Cited

U.S. PATENT DOCUMENTS 7,223,898 B2 *   5/2007   Rice ............................... 585/738

* cited by examiner

*Primary Examiner* — In Suk Bullock
*Assistant Examiner* — Sharon Pregler

(57) ABSTRACT

One exemplary embodiment can be a process for isomerizing a feed stream including one or more C4-C6 hydrocarbons. The process may include contacting the feed stream in an isomerization reaction zone with an isomerization catalyst at isomerization conditions to produce an isomerization zone effluent; passing at least a portion of the isomerization zone effluent to a stabilizer zone and recovering a stabilizer overhead stream, a bottom stream, and a stripper feed stream; passing the stripper feed stream to a stripping zone and separating the stripper feed stream into a stripper overhead stream and a stripper bottom stream; and recycling at least a portion of the stripper bottom stream to a deisopentanizer zone and passing a stream from the deisopentanizer zone to the isomerization reaction zone. Usually, the stabilizer overhead stream includes one or more $C5^-$ hydrocarbons, the bottom stream includes at least about 85%, by weight, one or more $C6^+$ hydrocarbons, and a stripper feed stream including at least about 10%, by weight, one or more $C5^+$ hydrocarbons. Often, a stripper overhead stream includes at least about 5%, by weight, one or more $C4^-$ hydrocarbons and a stripper bottom stream includes at least about 90%, by weight, one or more $C5^+$ hydrocarbons.

9 Claims, 2 Drawing Sheets

PROCESS FOR ISOMERIZING A FEED STREAM INCLUDING ONE OR MORE C4-C6 HYDROCARBONS

CROSS-REFERENCE TO RELATED APPLICATION

This application is a Division of copending application Ser. No. 13/005,940 filed Jan. 13, 2011, the contents of which are hereby incorporated by reference in its entirety.

FIELD OF THE INVENTION

This invention generally relates to a process for isomerizing, and more particularly, a process for isomerizing a feed stream including one or more C4-C6 hydrocarbons.

DESCRIPTION OF THE RELATED ART

Normally, a traditional gasoline blending pool includes $C4^+$ hydrocarbons having boiling points of less than about 205° C. at atmospheric pressure. This range of hydrocarbons may include C4-C6 paraffins and, particularly C5-C6 normal paraffins that can have relatively low octane numbers. To improve octane, isomerization may rearrange the structure of the paraffinic hydrocarbons into branched-chain paraffins. Often, octane upgrading commonly uses isomerization to convert C6 and lighter boiling hydrocarbons.

Typically, isomerization units for C5 and C6 hydrocarbons may have a high C5 content that may limit octane, particularly if the equilibrium C5 isomerization ratio is reached in the reactor. Usually, a deisopentanizer column can be positioned in front of the isomerization unit to remove isomerized C5 hydrocarbons in the fresh feed allowing a higher conversion of the normal C5 hydrocarbons-rich isomerization reactor feed. However, the fresh feed normal pentane conversion to isopentane may be limited without recycling isomerized C5 hydrocarbons from the product. Utilization of sieves on the product can remove the normal pentane and permit their recycle, however such installations are generally capital intensive and require significant utilities. As a consequence, there is generally a desire to provide a mechanism that is less capital intensive and lowers utility utilization to permit the recycling of these materials.

SUMMARY OF THE INVENTION

One exemplary embodiment can be a process for isomerizing a feed stream including one or more C4-C6 hydrocarbons. The process may include contacting the feed stream in an isomerization reaction zone with an isomerization catalyst at isomerization conditions to produce an isomerization zone effluent; passing at least a portion of the isomerization zone effluent to a stabilizer zone and recovering a stabilizer overhead stream, a bottom stream, and a stripper feed stream; passing the stripper feed stream to a stripping zone and separating the stripper feed stream into a stripper overhead stream and a stripper bottom stream; and recycling at least a portion of the stripper bottom stream to a deisopentanizer zone and passing a stream from the deisopentanizer zone to the isomerization reaction zone. Usually, the stabilizer overhead stream includes one or more $C5^-$ hydrocarbons; the bottom stream includes at least about 85%, by weight, one or more $C6^+$ hydrocarbons; and a stripper feed stream including at least about 10%, by weight, one or more $C5^+$ hydrocarbons. Often, a stripper overhead stream includes at least about 5%, by weight, one or more $C4^-$ hydrocarbons and a stripper bottom stream includes at least about 90%, by weight, one or more $C5^+$ hydrocarbons.

Another exemplary embodiment may be a process for isomerizing a feed stream having one or more C4-C6 hydrocarbons. The process can include contacting the feed stream in an isomerization reaction zone with an isomerization catalyst at isomerization conditions to produce an isomerization zone effluent; passing at least a portion of the isomerization zone effluent to a stabilizer column and recovering a stabilizer overhead stream, and a bottom stream; passing the stabilizer overhead stream to a receiver; withdrawing a receiver bottom stream from the receiver and providing at least a portion as a stripper feed stream; and recycling a stripper bottom stream to a deisopentanizer zone and passing a stream from the deisopentanizer zone to the isomerization reaction zone. The stabilizer overhead stream may include one or more $C5^-$ hydrocarbons, and a bottom stream may include at least about 85%, by weight, one or more $C6^+$ hydrocarbons. The stripper feed stream can include at least about 10%, by weight, one or more $C5^+$ hydrocarbons, and the stripper bottom stream can include at least about 90%, by weight, one or more $C5^+$ hydrocarbons to a deisopentanizer zone.

Yet another exemplary embodiment can be a process for isomerizing a feed stream including one or more C4-C6 hydrocarbons. The process may include contacting the feed stream in an isomerization reaction zone with an isomerization catalyst at isomerization conditions to produce an isomerization zone effluent; passing at least a portion of the isomerization zone effluent to a stabilizer column and recovering a stabilizer overhead stream, a bottom stream, and a side-stream; passing at least a portion of the side-stream to a stripper column; and recycling a stripper bottom stream to a deisopentanizer zone and passing a stream from the deisopentanizer zone to the isomerization reaction zone. A stabilizer overhead stream may include one or more $C5^-$ hydrocarbons, a bottom stream may include at least about 85%, by weight, one or more $C6^+$ hydrocarbons, and a side-stream may include at least about 85%, by weight, one or more $C5^+$ hydrocarbons. Also, the stripper bottom stream can include at least about 90%, by weight, one or more $C5^+$ hydrocarbons.

Generally, the embodiments disclosed herein can allow the addition of a stripping zone to separate an isomerization zone effluent into separate streams. Particularly, a stripper overhead stream can include at least about 5%, by weight, one or more $C4^-$ hydrocarbons and a stripper bottom stream comprising at least 90%, by weight, one or more $C5^+$ hydrocarbons. The stripper bottom stream can be recycled to a deisopentanizer zone that can further separate isopentanes from normal pentanes. As a consequence, such a configuration can allow the efficient recycling of one or more C5 hydrocarbons, while minimizing the recycling of $C4^-$ hydrocarbons and allowing a recovery of normal pentanes for recycling through the isomerization zone. Thus, the embodiments disclosed herein can provide an improved process for recycling one or more C5 hydrocarbons in an isomerization zone without having an undue increase in energy and capital expenses.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three carbon atoms and/or more.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 50%, and preferably about 70%, by mole, of a compound or class of compounds in a stream.

As used herein, the term "substantially" can mean an amount of at least generally about 80%, and preferably about 90%, by mole, of a compound or class of compounds in a stream.

As used herein, the terms "alkane" and "paraffin" may be used interchangeably.

As used herein, the term "overhead stream" can mean a stream withdrawn at or near a top of a column, typically a distillation column.

As used herein, the term "bottom stream" can mean a stream withdrawn at or near a bottom of a column, typically a distillation column.

As depicted, process flow lines in the figures can be referred to, interchangeably, as, e.g., lines, pipes, streams, feeds, effluents, and products.

DETAILED DESCRIPTION

Figure 1:
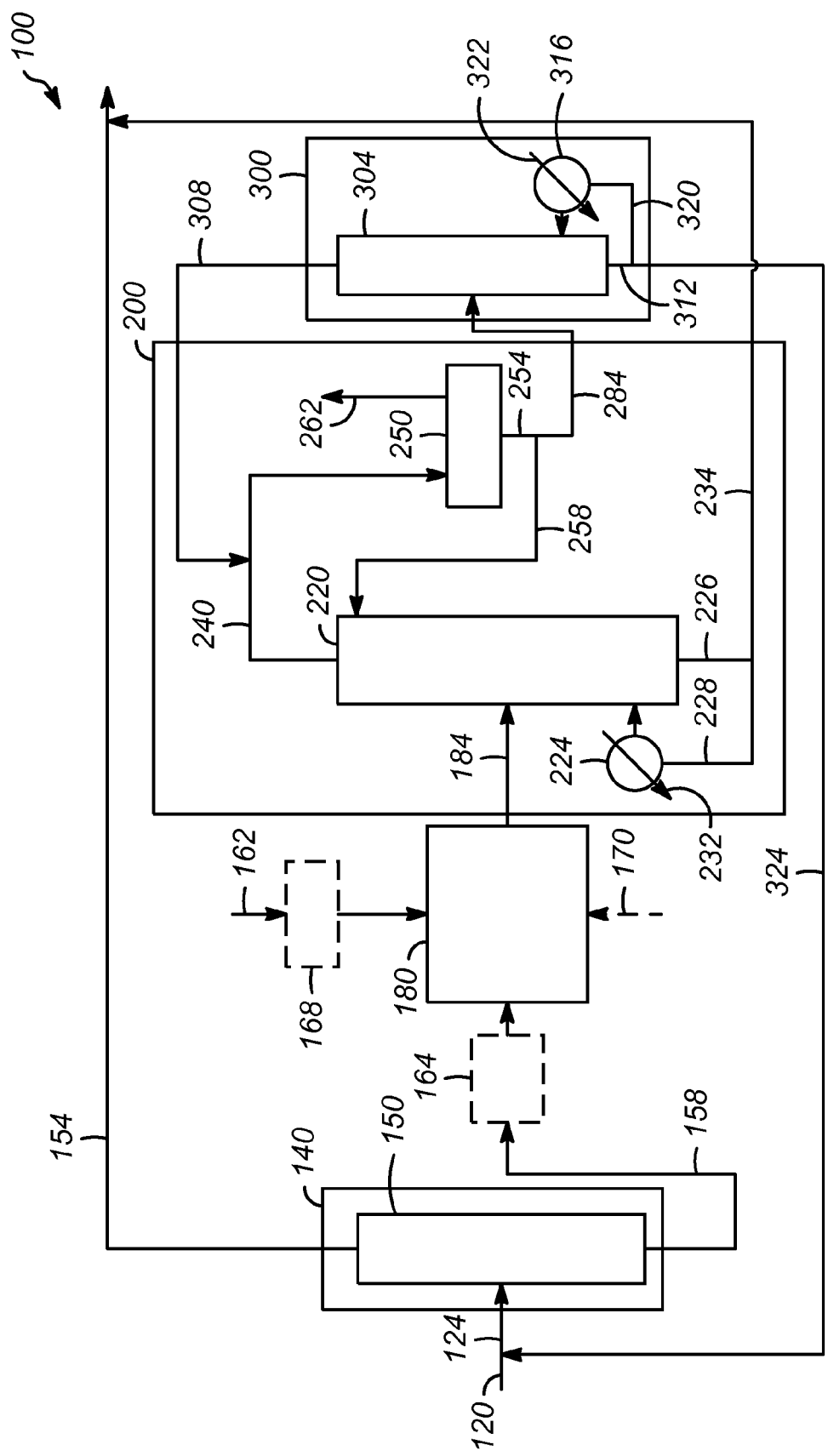
FIG. 1 is a schematic depiction of an exemplary isomerate manufacturing zone.

Referring to FIG. 1, an exemplary isomerate manufacturing zone 100 can include a deisopentanizer zone 140, an isomerization reaction zone 180, a stabilizer zone 200, and a stripping zone 300. Zones for isomerizing C4-C6 hydrocarbons are disclosed in, e.g., Nelson A. Cusher, *UOP Penex Process* and *UOP Par-Isom Process*, The Handbook of Petroleum Refining Processes, 3rd edition, Robert A. Myers, editor, 2004, pp. 9.15-9.27 and pp. 9.41-9.45, as well as, e.g., U.S. Pat. No. 5,326,926, U.S. Pat. No. 7,223,898 B2, and U.S. Pat. No. 7,514,590 B1.

A feed stream 120 can include a hydrocarbon fraction having one or more C4-C6 normal paraffins. Such hydrocarbon fractions are disclosed in, e.g., U.S. Pat. No. 7,223,898 B2. The hydrocarbon fractions can include C4-C6 normal paraffins, and optionally rich in C4-C6 normal paraffins. One exemplary hydrocarbon fraction has substantially pure normal paraffins having from 4-6 carbon atoms. Other hydrocarbon fractions may include a light natural gasoline, a light straight run naphtha, a gas oil condensate, a light raffinate, a light reformate, a light hydrocarbon, a field butane, and a straight-run distillate having distillation end points of about 77° C. and optionally containing substantial quantities of one or more C4-C6 paraffins. The feed stream 120 may also contain low concentrations of unsaturated hydrocarbons and hydrocarbons having more than 6 carbon atoms.

In one exemplary embodiment, the feed stream 120 can include:

TABLE 1

| | (in percent, by weight) | | | |
|---|---|---|---|---|
| RANGE | C4− | C5 | C6 | C7+ |
| General | 0-2 | 10-90 | 10-90 | 0-15 |
| Typical | 0.5 | 40-60 | 40-60 | 2 |

The feed stream 120 can be combined with a recycle stream 324, as hereinafter described, to form a combined feed 124, and its composition may vary among chemical manufacturing plants and refineries. The combined feed 124 can be provided to a deisopentanizer zone 140. Generally, the deisopentanizer zone 140 can include a deisopentanizer column 150. The deisopentanizer column 150 can provide an overhead stream 154 including at least about 85%, by weight, one or more C5 hydrocarbons, such as isopentane, which can be utilized as an isomerate product. The bottom stream 158 from the deisopentanizer zone 140 can be provided to the isomerization reaction zone 180.

If a halided, such as a chlorided, catalyst is utilized, the bottom stream 158 can pass through a dryer 164 before entering the isomerization reaction zone 180. Typically, the isomerization reaction zone 180 can also receive a make-up gas stream 162 that may pass through a dryer 168 and a chloride stream 170. An exemplary isomerization reaction zone 180 is disclosed in, e.g., U.S. Pat. No. 7,223,898. In such an isomerization reaction zone 180, the gas often separated in the stabilizer zone 200, as hereinafter described, can be scrubbed prior to being discharged.

The isomerization reaction zone 180 can include one or more exemplary catalysts disclosed in, e.g., U.S. Pat. No. 7,223,898 B2 and U.S. Pat. No. 5,326,926. The combined feed 124 may be contacted in the isomerization reaction zone 180 with an isomerization catalyst. Such a catalyst can be a halided catalyst, such as a chlorided platinum alumina catalyst. The alumina can be an anhydrous gamma-alumina, although other aluminas may be utilized. In addition to platinum, the catalyst may optionally include one or more of palladium, germanium, ruthenium, rhodium, osmium, and iridium. The catalyst may contain from about 0.1-about 0.25%, by weight, platinum, and optionally about 0.1-about 0.25%, by weight, one or more of palladium, germanium, ruthenium, rhodium, osmium, and iridium, based on the weight of the catalyst. Such an exemplary catalyst is disclosed in, e.g., U.S. Pat. No. 5,326,926.

If a non-halided catalyst is utilized, the dryers 164 and 168 and the chloride stream 170 can be omitted. Particularly, the bottom stream 158 can proceed directly to the isomerization reaction zone 180 without drying. In addition, the make-up gas stream 162 can also pass directly to the isomerization zone absent drying. Catalysts incorporated in such zones are disclosed in, e.g., U.S. Pat. No. 7,223,898 B2.

Another suitable isomerization catalyst is a solid strong acid catalyst, which may include a sulfated support of an oxide or hydroxide of a Group IVB (IUPAC 4) metal, preferably a zirconium oxide or hydroxide, at least a first component of a lanthanide element or yttrium, and at least a second component being a platinum-group metal component. The Group IVB (IUPAC 4) metal may include titanium, zirconium, halfnium, and dubnium. The catalyst optionally contains an inorganic-oxide binder, such as alumina.

The support material of the solid strong acid catalyst can include an oxide or a hydroxide of a Group IVB (IUPAC 4) metal. In one exemplary embodiment, the Group IVB element is zirconium or titanium. Sulfate may be composited on the support material. A component of a lanthanide-series element can be incorporated into the composite using any suitable means. The lanthanide series element component may be one or more of lanthanum, cerium, praseodymium, neodymium, promethium, samarium, europium, gadolinium, terbium, dysprosium, holmium, erbium, thulium, ytterbium and lutetium. A suitable amount of the lanthanide series component may be about 0.01-about 10%, by weight, on an elemental basis, based on the weight of the catalyst. A platinum-group metal component may be added to the catalytic composite by any suitable means, such as impregnation. The platinum-group metal component may be one or more of platinum, palladium, ruthenium, rhodium, iridium, and osmium, in an amount of about 0.01-about 2%, by weight, of the platinum-group metal component, on an elemental basis based on the weight of the catalyst.

Optionally, the catalyst is bound with a refractory inorganic oxide. The binder, when employed, usually comprises from about 0.1-about 50%, preferably about 5-about 20%, by weight, based on the weight of the finished catalyst. The support, sulfate, metal components and optional binder may be composited in any order effective to prepare a catalyst useful for the isomerization of hydrocarbons. Examples of suitable atomic ratios of lanthanide or yttrium to platinum-group metal may be at least about 1:1; preferably about 2:1. Optionally, the catalyst may further include a third component of iron, cobalt, nickel, rhenium or a mixture thereof. As an example, iron may be present in an amount of about 0.1-about 5%, by weight, on an elemental basis based on the weight of the catalyst. In one exemplary embodiment, the solid strong acid isomerization catalyst may be sulfated zirconia or a modified sulfated zirconia.

The isomerization reaction zone 180 can operate at any suitable conditions depending on the composition of the combined feed 124 and catalyst type. As an example, operating conditions within the isomerization reaction zone 180 may be selected to maximize the production of isoalkanes. A temperature within the isomerization reaction zone 180 usually ranges from about 40-about 235° C. and a pressure usually ranges from about 700-7,000 KPa. The feed rate to the isomerization reaction zone 180 can also vary over a wide range, including a liquid hourly space velocity ranging from about 0.5-about 12 hr$^{-1}$.

The isomerization effluent 184 may be sent to the stabilizer zone 200 to separate the desired isomerized products from hydrogen, light ends, lower octane isomerized products, and cyclohexane plus heavy hydrocarbons having 7 or more carbon atoms. The stabilizer zone 200 can include a stabilizer column 220, a receiver 250 and a reboiler 224. The stabilizer column 220 can operate under suitable conditions for providing a C5 recycle stream to the deisopentanizer zone 140. In this manner, the following table discloses typical operating parameters for one exemplary embodiment having the stabilizer column 220 in conjunction with an isomerization reaction zone 180 containing a non-halided catalyst:

TABLE 2

| Parameter | General | Preferred | Optimal |
| --- | --- | --- | --- |
| Operating Pressure (kPa) | 790-2,100 | 1,100-1,500 | 1,200-1,420 |
| Bottoms Temperature (° C.) | 140-210 | 170-200 | Not Applicable |
| Stabilizer Trays | 25-75 | 35-60 | 40-50 |
| Stabilizer Reflux/Feed Molar Ratio | 0.5-3 | 1.0-2.5 | 1.5-2.0 |

The stabilizer bottoms temperature may change significantly due to the presence of heavier hydrocarbons, such as C7$^-$ hydrocarbons, present in the feed, i.e., isomerization zone effluent 184 to the stabilizer column 220.

Typically, the stabilizer column 220 can produce an overhead stream 240 that may pass to the receiver 250, where one or more C5$^-$ hydrocarbons may separate as a gas stream 262 and be scrubbed for a halided isomerization catalyst or recycled for a non-halided isomerization catalyst. A receiver bottom stream 254 can be split into a reflux stream 258 and a stripper feed 284, which will be described hereinafter. A bottom stream 226 from the stabilizer column 220 can be split into a reboiling stream 228 and a product stream 234. The reboiling stream 228 can pass through the reboiler 224 and be heated with any suitable heating stream 232, such as a pressurized steam or a process stream. Typically, the bottom stream 226 can include at least about 85%, by weight, one or more C6$^+$ hydrocarbons. The product stream 234 can be combined with the overhead stream 154 from the deisopentanizer zone 140 to form a combined product for, e.g., a gasoline blending pool.

The stripper feed 284, which may be a portion from the receiver bottom stream 254 of the receiver 250, can pass to the stripping zone 300. The stripper feed 284 can include at least about 10%, by weight, one or more C5$^1$ hydrocarbons. The stripping zone 300 can include a stripper column 304 having a reboiler 316 that can provide a stripper overhead stream 308 and a stripper bottom stream 312. Generally, the stripper overhead stream 308 includes at least about 5%, by weight, one or more C4$^-$ hydrocarbons. The stripper overhead stream 308 can be combined with the stabilizer overhead stream 240 that is provided to the receiver 250 and may include at least about 10%, by weight, one or more C5$^-$ hydrocarbons. The stripper bottom stream 312 can be split into a stripper reboiling stream 320 and the net stripper bottom stream or stripper recycle stream 324 and include at least about 90%, by weight, one or more C5$^+$ hydrocarbons. Typically, the stripper column 304 is operated to provide the stripper recycle stream 324 that has low levels of C4$^-$ hydrocarbons. As depicted, the stripper column 304 typically includes the reboiler 316, but may not include a condenser and a receiver.

In this manner, the following table discloses typical operating parameters for one exemplary embodiment having the stripper column 304 in conjunction with an isomerization reaction zone 180:

TABLE 3

| Parameter | General | Preferred |
| --- | --- | --- |
| Bottoms Temperature (° C.) | 115-160 | 130-145 |
| Stripper Column Trays | 5-30 | 10-20 |

The stripper reboiling stream 320 can pass through the reboiler 316 which can be provided with a heating stream 322. The heating stream 322 can use any suitable heat source, such as another process stream or a pressurized steam. The stripper reboiling stream 320 can be returned to the stripper column 304.

Exemplary compositions for streams in the isomerate manufacturing zone 100 as depicted in FIG. 1 can be as follows:

TABLE 4

(in percent, by weight, based on weight of the stream)

| Stream | Range | $C4^-$ | Total C5 | iC5 | nC5 | C6 | $C7^+$ |
|---|---|---|---|---|---|---|---|
| 154 | General | 0-5 | — | 85-99.5 | 0.1-15 | <0.1 | <0.1 |
|  | Typical | 1 | — | 95 | 5 | <0.1 | <0.1 |
| 158 | General | <0.1 | — | 1-10 | 10-80 | 10-95 | 0-15 |
|  | Typical | <0.1 | — | 2-3 | 30-60 | 40-70 | 2-5 |
| 262 | General | 80-98 | 2-20 | — | — | — | — |
|  | Typical | 90-95 | 5-10 | — | — | — | — |
| 284 | General | 50-80 | — | 10-30 | 2-10 | 1-3 | <0.1 |
|  | Typical | 65-75 | — | 18-23 | 4-8 | 1-2 | <0.1 |
| 324 | General | 0.5-4 | — | 60-80 | 15-25 | 2-15 | <0.1 |
|  | Typical | 0.8-1.2 | — | 65-75 | 20-25 | 4-8 | <0.1 |
| 234 | General | 0-2 | 0-10 | — | — | 80-95 | 1-10 |
|  | Typical | <0.1 | 0-5 | — | — | 92-94 | 2-5 |

Figure 2:
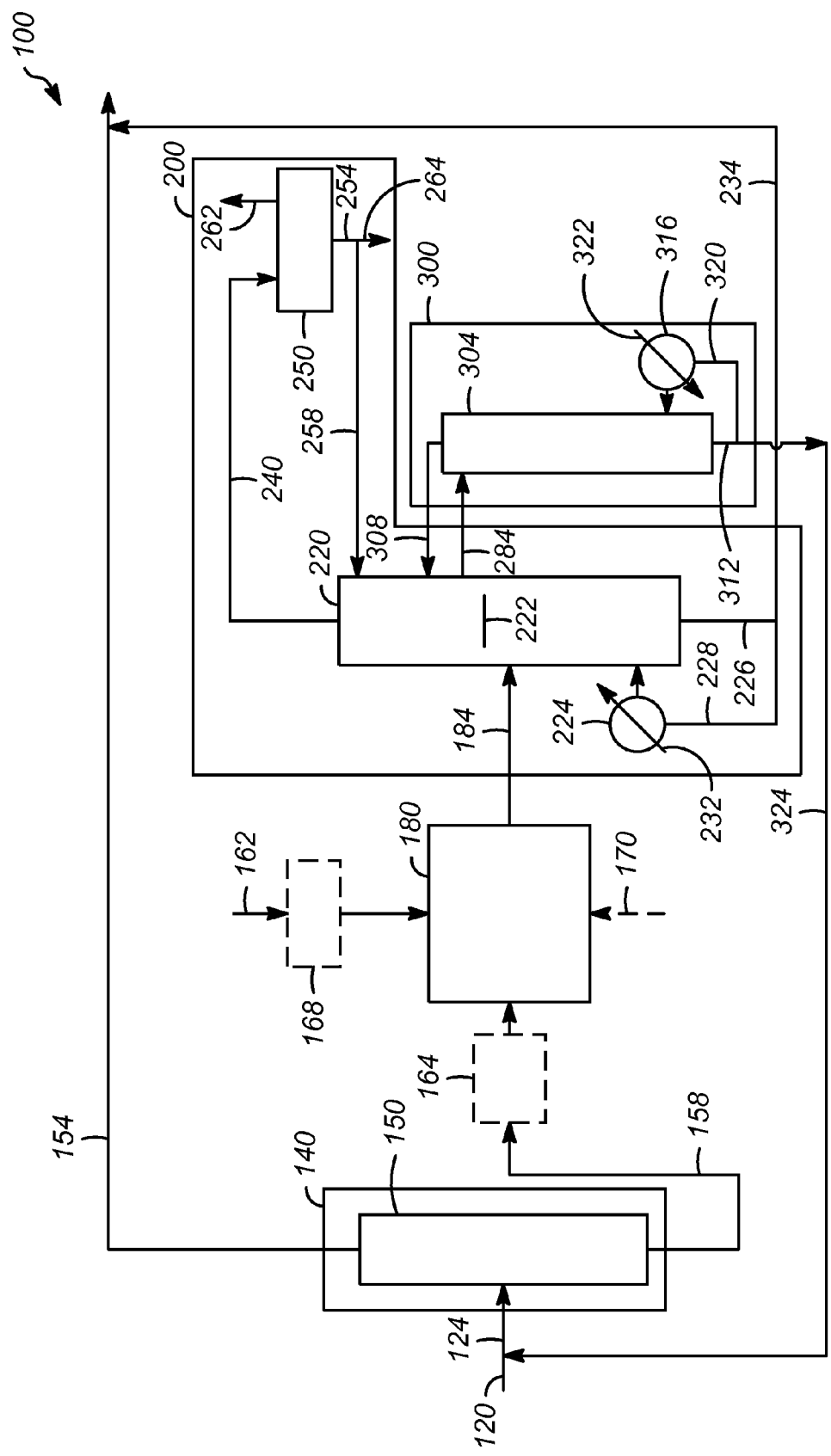
FIG. 2 is a schematic depiction of another version of the exemplary isomerate manufacturing zone.

Referring to FIG. 2, another exemplary version of the isomerate manufacturing zone 100 is depicted. In this exemplary embodiment, the stripping zone 300 receives a stripper feed 284 as a side-stream from the stabilizer column 220. As discussed above in FIG. 1, an isomerization zone effluent 184 can be provided to the stabilizer zone 200. The isomerization zone effluent 184 is provided to the stabilizer column 220 and produces the stabilizer overhead stream 240 and the bottom stream 226. The stabilizer overhead stream 240 passes to the receiver 250 and provides a gas stream 262 that can be scrubbed or recycled as discussed above, and the receiver bottom stream 254. A portion of the receiver bottom stream 254 can be removed as a stream 264 with another portion provided as the reflux stream 258. Any suitable tray within the stabilizer column 220, typically within the top two-fifths, or even top third, of the trays in the stabilizer column 220, can have the stripper feed 284 withdrawn as a side-stream from a tray 222. The stripper feed 284 may be provided to the stripper column 304, as discussed above, and may include at least about 10%, or even at least about 70% or about 85%, by weight, one or more $C5^+$ hydrocarbons. Generally, the purpose of the stripper column 304 is to strip $C4^-$ hydrocarbons to provide the net stripper bottom stream 324 containing predominantly C5 one or more hydrocarbons for recycling to the isomerization reaction zone 180. Usually, the stripper overhead stream 308 can be returned to the stabilizer column 220 while the stripper bottom stream 312 is split as the stripper reboiling stream 320 and the stripper recycle stream 324, which is combined with the feed stream 120. The bottoms of the stabilizer column 220 may operate as discussed above. In this exemplary embodiment, withdrawing the side-stream can allow the separation of C5 hydrocarbons for recycling to the isomerization reaction zone 180. Moreover, utilizing the recycle to the deisopentanizer zone 140 can remove isopentane before the bottom stream 158 enters the isomerization reaction zone 180. Although not depicted in the drawings, all columns depicted may be associated with other equipment, such as reboilers, condensers, and heat exchangers.

In operation, it is generally desired to operate the stabilizer column 220 and the stripper column 304 at such conditions to provide the maximum amount of C5 hydrocarbons to the combined feed 124. Exemplary operating conditions for stabilizer column 220 and the stripper column 304 are depicted above.

Exemplary compositions for streams in the isomerate manufacturing zone 100 as depicted in FIG. 2 without stream 264 can be as follows:

TABLE 5

(in percent, by weight, based on weight of the stream)

| Stream | Range | $C4^-$ | Total C5 | iC5 | nC5 | C6 | $C7^+$ |
|---|---|---|---|---|---|---|---|
| 154 | General | 0-5 | — | 85-99.5 | 0.1-15 | <0.1 | <0.1 |
|  | Typical | 1 | — | 95 | 5 | <0.1 | <0.1 |
| 158 | General | <0.1 | — | 1-10 | 10-80 | 10-95 | 0-15 |
|  | Typical | <0.1 | — | 2-3 | 30-60 | 40-70 | 2-5 |
| 262 | General | 80-98 | 2-20 | — | — | — | — |
|  | Typical | 90-95 | 5-10 | — | — | — | — |
| 284 | General | 1-15 | — | 60-80 | 10-30 | 1-15 | <0.1 |
|  | Typical | 3-9 | — | 65-75 | 16-22 | 2-7 | <0.1 |
| 324 | General | 0.5-5 | — | 60-80 | 10-30 | 2-15 | <0.1 |
|  | Typical | 0.5-2 | — | 65-75 | 18-25 | 4-8 | <0.1 |
| 234 | General | <0.1 | 0-10 | — | — | 80-95 | 1-10 |
|  | Typical | <0.1 | 0-5 | — | — | 92-94 | 2-5 |

Exemplary compositions for streams in isomerate manufacturing zone 100 as depicted in FIG. 2 with stream 264 can be as follows:

TABLE 6

(in percent, by weight, based on weight of the stream)

| Stream | Range | $C4^-$ | Total C5 | iC5 | nC5 | C6 | $C7^+$ |
|---|---|---|---|---|---|---|---|
| 154 | General | 0-5 | — | 85-99.5 | 0.1-15 | <0.1 | <0.1 |
|  | Typical | 1 | — | 95 | 5 | <0.1 | <0.1 |
| 158 | General | <0.1 | — | 1-10 | 10-80 | 10-95 | 0-15 |
|  | Typical | <0.1 | — | 2-3 | 30-60 | 40-70 | 2-5 |
| 262 | General | 95-100 | 0-5 | — | — | — | — |
|  | Typical | 98-99.5 | 0-2 | — | — | — | — |
| 284 | General | 1-15 | — | 60-80 | 10-30 | 1-15 | <0.1 |
|  | Typical | 3-8 | — | 68-78 | 15-25 | 2-7 | <0.1 |
| 324 | General | 0.5-5 | — | 60-80 | 10-30 | 1-15 | <0.1 |
|  | Typical | 0.5-2 | — | 68-78 | 15-25 | 2-8 | <0.1 |
| 234 | General | <0.1 | 0-15 | — | — | 80-95 | 1-10 |
|  | Typical | <0.1 | 2-8 | — | — | 90-94 | 2-5 |
| 264 | General | 90-100 | 0-10 | — | — | <0.1 | <0.1 |
|  | Typical | 97-99 | 1-3 | — | — | <0.1 | <0.1 |

In this exemplary embodiment with a non-halided catalyst, there is typically no need to remove halide compounds such as hydrogen chloride. As a result, the stream 264 may be taken as a product.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for isomerizing a feed stream comprising one or more C4-C6 paraffins, comprising:
   A) contacting the feed stream in an isomerization reaction zone with an isomerization catalyst at isomerization conditions to produce an isomerization zone effluent;
   B) passing at least a portion of the isomerization zone effluent to a stabilizer zone and recovering a stabilizer overhead stream comprising one or more $C5^-$ hydrocarbons, a bottom stream comprising at least about 85% by weight one or more $C6^+$ hydrocarbons, and a side stream comprising at least about 85% by weight one or more $C5^+$ hydrocarbons;
   C) passing at least a portion of the side stream to a stripping zone and separating the side stream into a stripper overhead stream comprising at least about 5% by weight one or more $C4^-$ hydrocarbons and a stripper bottom stream comprising at least about 90% by weight one or more $C5^+$ hydrocarbons; and
   (D) passing at least a portion of the stripper bottom stream to a deisopentanizer zone comprising a deisopentanizer column; and
   (E) passing a bottoms stream from the deisopentanizer zone to the isomerization reaction zone.

2. The process according to claim 1, wherein the isomerization reaction zone comprises a chlorided platinum alumina catalyst or a sulfated zirconia catalyst.

3. The process according to claim 1, wherein the isomerization reaction zone comprises a catalyst, in turn, comprising a support comprising a sulfated oxide or hydroxide of at least one element of titanium, zirconium, hafnium, and dubnium; a first component of at least one element of a lanthanide series and yttrium; and a second component of at least one element of platinum, palladium, ruthenium, rhodium, iridium, and osmium.

4. The process according to claim 1, wherein the isomerization reaction zone comprises a catalyst, in turn, comprising an alumina, a platinum, and a chloride.

5. The process according to claim 1, wherein the stripping zone comprises a stripper column, and the stripper bottom stream upon exiting the stripper column is at a temperature of about 115-about 160° C.

6. The process according to claim 5, wherein the stabilizer zone comprises a stabilizer column, and the bottom stream exiting the stabilizer column is at a temperature of about 140-about 210° C.

7. The process according to claim 6, wherein the stabilizer column operates at a pressure of about 790-about 2,100 kPa.

8. The process according to claim 1, wherein the process further comprises withdrawing an overhead stream comprising at least about 85%, by weight, one or more C5 hydrocarbons from the deisopentanizer column.

9. The process according to claim 1, wherein the stripper bottom stream upon exiting the stripper column is at a temperature of about 115-about 160° C.

* * * * *